US006923070B2

United States Patent
Workman

(12) United States Patent
(10) Patent No.: US 6,923,070 B2
(45) Date of Patent: Aug. 2, 2005

(54) UNBONDED SYSTEM FOR STRENGTH TESTING OF CONCRETE CYLINDERS

(75) Inventor: Gary Workman, Lombard, IL (US)

(73) Assignee: Deslauriers, Inc., Broadview, IL (US)

( * ) Notice: Subject to any disclaimer, the term of this patent is extended or adjusted under 35 U.S.C. 154(b) by 0 days.

(21) Appl. No.: 10/712,940

(22) Filed: Nov. 13, 2003

(65) Prior Publication Data
US 2005/0103118 A1 May 19, 2005

(51) Int. Cl.[7] ............................................... G01N 3/00
(52) U.S. Cl. ....................................................... 73/803
(58) Field of Search ........................ 73/808, 818, 821, 73/824

(56) References Cited

U.S. PATENT DOCUMENTS

| | | |
|---|---|---|
| 2,414,559 A | 1/1947 | Patch et al. |
| 3,545,263 A | 12/1970 | Hedley et al. |
| 4,445,387 A | 5/1984 | Hall et al. |
| 4,740,025 A | 4/1988 | Nelson |
| 5,677,495 A * | 10/1997 | Johnson et al. ................ 73/856 |
| 6,591,691 B2 | 7/2003 | Kim et al. |
| 6,832,524 B2 * | 12/2004 | Workman ...................... 73/803 |

OTHER PUBLICATIONS

"Econ-O-Cap" Product Guide, Deslauriers, Inc.

* cited by examiner

Primary Examiner—Max Noori
(74) Attorney, Agent, or Firm—Wood, Phillips, Katz, Clark & Mortimer

(57) ABSTRACT

An unbonded capping system for compression testing of concrete cylinders comprises first and second retaining cups comprising metal blocks each having opposite parallel planar surfaces. A first of the planar surfaces is engageable by a test apparatus, in use. A second of the planar surfaces has a cylindrical cavity of a first select diameter for receiving one end of the concrete cylinder. First and second cylindrical compression pads are each to be received in one of the retaining cup cavities to abut an end of the concrete cylinder, in use. The compression pads are of a second select diameter smaller than the first select diameter of the cavity to define a circumferential space therebetween. Nubs are provided for gripping the cavity to prevent the compression pads from falling out of the cavities.

20 Claims, 2 Drawing Sheets

UNBONDED SYSTEM FOR STRENGTH TESTING OF CONCRETE CYLINDERS

FILED OF THE INVENTION

This invention relates to compression testing of concrete samples and, more particularly, to an unbonded capping system.

BACKGROUND OF THE INVENTION

Various tests have been developed to ensure that concrete used in particular applications satisfies specifications. One of these is a compression test for testing concrete cylinders. Initially, the tests were performed by capping freshly molding concrete cylinders with materials such as sulfur mortar. This provides a smooth, hard surface which fills any imperfections which normally occur when making the concrete cylinder. These procedures require considerable preparation time.

More recently, unbonded capping systems have been developed. A typical unbonded capping system comprises a pair of retaining cups and a pair of compression pads. Each retaining cup retains one of the compression pads and fits over one end of the concrete cylinder. This assembly is then placed between the platens of a compression testing apparatus which compresses the sample to failure. The compression pad, which is made of a tough elastomeric material, flows into irregularities in the concrete cylinder and distributes the test load uniformly without creating air pockets to assure consistent breaks. The tests for using unbonded caps are specified in ASTM Standard C1231 and AASHTO Standard T22. Under both standards the compression pad has a smaller outer diameter than an inner diameter of the retaining cup. As a result, there is a circumferential space between the compression pad and the retaining cup. As a result, the compression pads frequently fall out of the retaining cups during test preparation.

The present invention is directed to further improvements in concrete cylinder compression testing.

SUMMARY OF THE INVENTION

In accordance with the invention, there is provided an unbonded capping system for compression testing of concrete samples.

In accordance with one aspect of the invention there is disclosed an unbonded capping system for compression testing of concrete cylinders comprising first and second retaining cups comprising metal blocks each having opposite parallel planar surfaces. A first of the planar surfaces is engageable by a test apparatus, in use. A second of the planar surfaces has a cylindrical cavity of a first select diameter for receiving one end of the concrete cylinder. First and second cylindrical compression pads are each to be received in one of the retaining cup cavities to abut an end of the concrete cylinder, in use. The compression pads are of a second select diameter smaller than the first select diameter of the cavity to define a circumferential space therebetween. Means are provided for gripping the cavity to prevent the compression pads from falling out of the cavities.

It is a feature of the invention that the compression pads comprise one piece neoprene pads.

It is another feature of the invention that the compression pads include a cylindrical sidewall of the second select diameter and the gripping means comprises a plurality of circumferentially spaced nubs extending radially outwardly from the sidewall. The first select diameter may be about 1/16 of an inch larger than the second select diameter. The nubs may have a height in a range of about 0.05 to 0.06 inches and may be about 1/16 of an inch.

There is disclosed in accordance with another aspect of the invention compression pads for use with an unbonded capping system for compression testing of concrete cylinders. The compression pads comprise a cylindrical block of elastomeric material having a cylindrical sidewall, to be received in a retaining cup cavity to abut an end of a concrete cylinder, in use. The sidewall is of a second select diameter smaller than a first select diameter of the cavity to define a circumferential space therebetween. Means are provided for gripping the retaining cup to prevent the compression pad from falling out of the cavity.

There is disclosed in accordance with yet another aspect of the invention an improvement in an unbonded capping system for compression testing of concrete cylinders, comprising retaining cups comprising metal blocks having a cylindrical cavity of a first select diameter for receiving one end of the concrete cylinder, and cylindrical compression pads each to be received in one of the retaining cup cavities to abut an end of the concrete cylinder, in use, and being of a second select diameter smaller than the first select diameter of the cavity to define a circumferential space therebetween. The improvement comprises means operatively associated with the compression pads for gripping the retaining cup cavity to prevent the compression pads from falling out of the cavities.

Further features and advantages of the invention will be readily apparent from the specification and from the drawings.

DETAILED DESCRIPTION OF THE INVENTION

Figure 1:
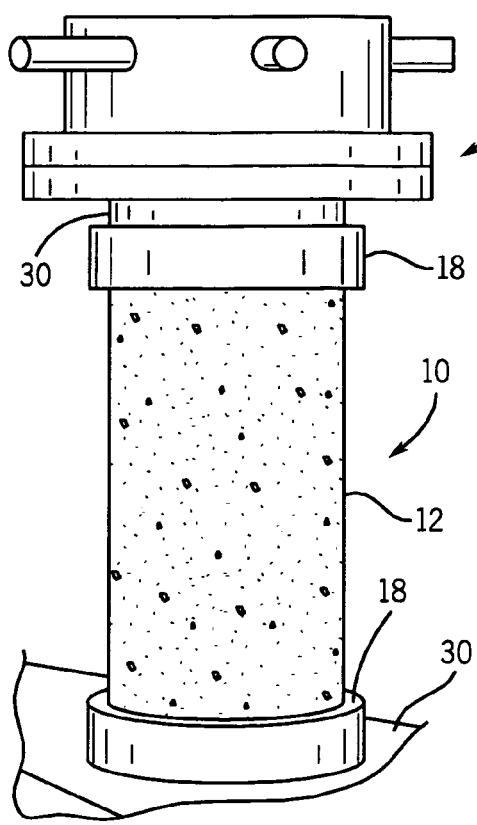
FIG. 1 is a perspective view of an unbonded capping system in accordance with the invention for compression testing of a concrete cylinder sample.
Figure 2:
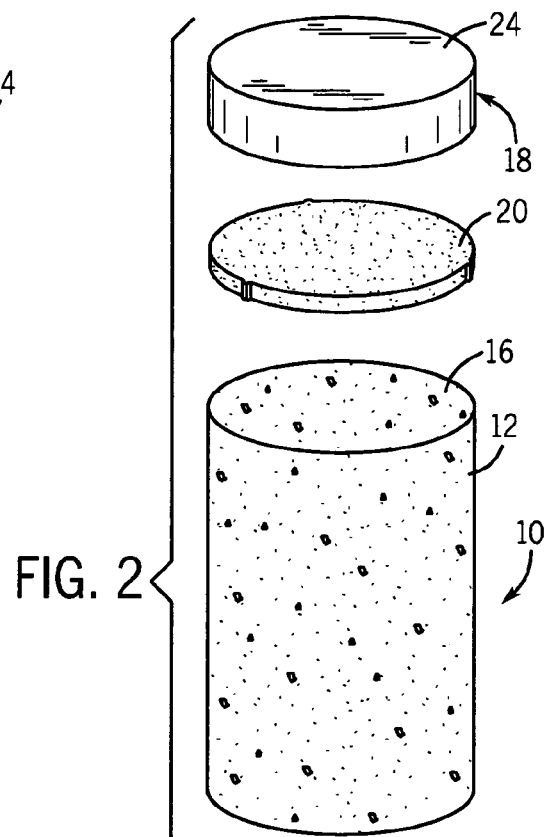
FIG. 2 is an exploded view of the unbonded capping system of FIG. 1 without the testing fixture.

In accordance with the invention, there is provided an unbonded capping system 10, see FIGS. 1 and 2, for compression testing of a concrete cylinder 12. The unbonded capping system 10 is adapted to be used with a compression testing apparatus or fixture 14, see FIG. 1.

The concrete cylinder 12 can be formed using any known technique. Conventionally, an end wall 16 of the concrete cylinder 12 is approximately six inches in diameter. The height of the concrete cylinder 12 is approximately twelve inches. Alternatively, the concrete cylinder 12 may be four inches in diameter and eight inches long. As is apparent, depending on the procedure used for forming the concrete cylinder 12, the exact dimensions may vary.

The unbonded capping system 10 comprises first and second retaining cups 18 and first and second compression pads 20. Each of the retaining cups 18 is identical in construction. Similarly, each compression paid 20 is identical in construction.

Each retaining cup 18 comprises a metal cylindrical block 22 having opposite parallel planar surfaces 24 and 26 defining end walls. The second planar surface 26 includes a cylindrical cavity 28, see FIG. 2. Each retaining cup 18 may be machined from high alloy steel to the same tolerance as platens 30 of the testing apparatus 14, see FIG. 1. The high alloy steel has minimal temperature variation and no deflection under loads. The high strength alloy steel retaining cups 18 resist scratching, thus eliminating the need for additional machining. In the illustrated embodiment of the invention, each retaining cup 18 is adapted for use with a six inch concrete cylinder and has an outer diameter of about 7.25 inches and a height of about 1.5 inches. The cavity 28 is about 6 3/16 inches in diameter with a depth of about 1 inch. Particularly, the cavity 28 is adapted to be larger in proportion than the desired size of the concrete cylinder end walls 16, which are seldom true in dimension and in squareness.

Figure 3:
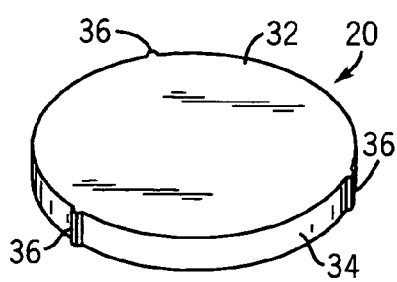
FIG. 3 is a perspective view of a compression pad for use with the unbonded capping system of FIG. 1.
Figure 4:
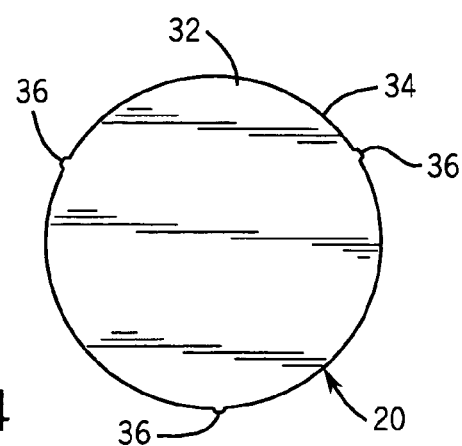
FIG. 4 is a top plan view of the compression pad of FIG. 3.

Referring also to FIGS. 3 and 4, the compression pad 20 comprises a cylindrical block 32 of a tough elastomeric material. The elastomeric material may be, for example neoprene. The block 32 includes a cylindrical sidewall 34. The pad 20 is about ½ of an inch thick and has a diameter of about 6 1/8 inches. In accordance with the invention, three nubs 36 extend radially outwardly from the sidewall 34. The nubs 36 are equally spaced about 120° apart. The nubs 36 may be about 0.12 inch to 0.125 inches wide and about 0.05 inch to 0.065 inches deep and may be on the order of 1/16 inches high.

The compression pads 20 have a hardness in the range of about 50 to 70 durometer.

Figure 5:
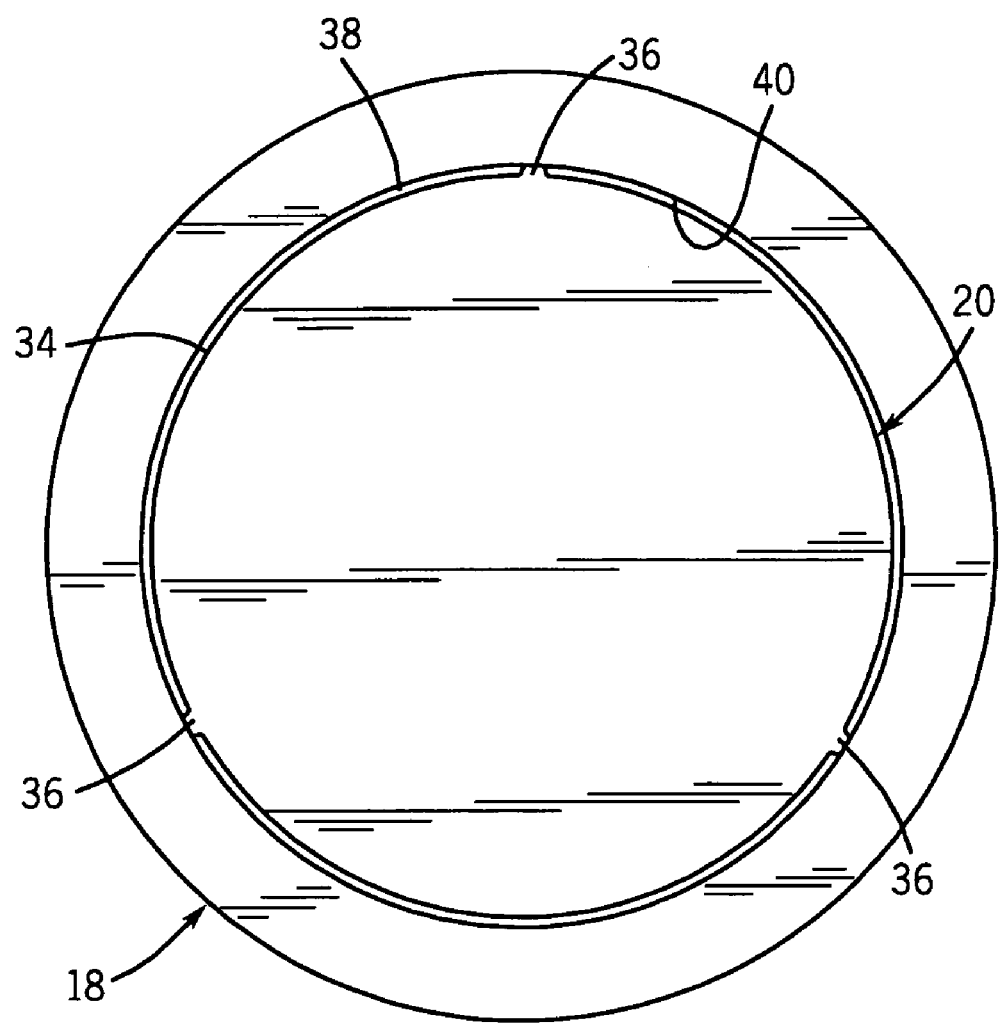
FIG. 5 is a top plan view illustrating the compression pad in accordance with the invention mounted in a retaining cup for the system of FIG. 1.

Referring to FIG. 5, the compression pad 20 is shown mounted in the retaining cup 18. As described above, the inner diameter of the cavity 28 is greater than the outer diameter of the compression pad sidewall 34 to define a circumferential space 38 therebetween. In the illustrated embodiment of the invention, the diameter of the pad 20 is 1/16 inch smaller than the inner diameter of the cavity 28 so that the circumferential space is about 1/32 inch at any given point. In accordance with the invention, the nubs 36 fully span the circumferential space 38 to engage a cavity sidewall 40. Particularly, the nubs 36 grip the retaining cup cavity sidewall 40 to prevent the compression pad 20 from falling out of the cavity 28.

As is apparent, the dimensions of the retaining cup 18 and compression pad 20 would be different for testing different size cylinders, such as four inch cylinders. Likewise, other sizes could also be used. In either case, the compression pad 20 is adapted for gripping the retaining cup as described. Moreover, the illustrated embodiment of the invention, three nubs 36 are provided on the compression pad 20. As is apparent, additional nubs could be used, and the nubs could be equally spaced apart or differentially spaced apart, as necessary or desired. The use of three nubs provides sufficient gripping and positioning of the compression pad 20 without interfering with the specifications and standards for a compression pad noted above.

In use, the compression pads 20 are inserted in the cavities 28. A retaining cup 18 with the compression pads 20 is placed onto each end 16 of the concrete cylinder 12. This assembly is then placed in the compression testing apparatus 14, see FIG. 1. Particularly, the first planar surface 24 is engagable by one of the test platens 30. The specimen is compressed to failure in a conventional manner.

Thus, in accordance with the invention, there is described an unbonded capping system for compression testing of concrete cylinders.

I claim:

1. An unbonded capping system for compression testing of concrete cylinders, comprising:
   first and second retaining cups comprising metal blocks each having opposite parallel planar surfaces, a first of the planar surfaces being engagable by a test apparatus, in use, and a second of the planar surfaces having a cylindrical cavity of a first select diameter for receiving one end of the concrete cylinder; and
   first and second cylindrical compression pads each to be received in one of the retaining cup cavities to abut an end of the concrete cylinder, in use, and being of a second select diameter smaller than the first select diameter of the cavity to define a circumferential space therebetween, and comprising means for gripping the cavity to prevent the compression pads from falling out of the cavities.

2. The unbonded capping system of claim 1 wherein the first and second retaining cups are of high alloy steel construction.

3. The unbonded capping system of claim 1 wherein the first and second retaining cups are cylindrically shaped and the parallel planar surfaces define end walls.

4. The unbonded capping system of claim 1 wherein the first and second compression pads comprise one piece neoprene pads.

5. The unbonded capping system of claim 1 wherein the first and second compression pads each comprises a cylindrical sidewall of the second select diameter and the gripping means comprises a plurality of circumferentially spaced nubs extending radially outwardly from the sidewall.

6. The unbonded capping system of claim 5 wherein the first select diameter is about 1/16 of an inch larger than the second select diameter.

7. The unbonded capping system of claim 6 wherein the nubs have a height of about 1/16 of an inch.

8. The unbonded capping system of claim 6 wherein the nubs have a height in a range of about 0.05 to 0.065 inches.

9. For use with an unbonded capping system for compression testing of concrete cylinders, including first and second retaining cups comprising metal blocks each having opposite parallel planar surfaces, a first of the planar surfaces being engagable by a test apparatus, in use, and a second of the planar surfaces having a cylindrical cavity of a first select diameter for receiving one end of the concrete cylinder, first and second compression pads each comprising:
   a cylindrical block of elastomeric material having a cylindrical sidewall, to be received in one of the retaining cup cavities to abut an end of the concrete cylinder, in use, the sidewall being of a second select diameter smaller than the first select diameter of the cavity to define a circumferential space therebetween, and comprising means for gripping the retaining cup to prevent the compression pad from falling out of the cavity.

10. The compression pads of claim 9 wherein the first and second compression pads comprise one piece neoprene pads.

11. The compression pads of claim 9 wherein the gripping means comprises a plurality of circumferentially spaced nubs extending radially outwardly from the sidewall.

12. The compression pads of claim 11 wherein the first select diameter is about 1/16 of an inch larger than the second select diameter.

13. The compression pads of claim 12 wherein the nubs have a height of about 1/16 of an inch.

14. The compression pads of claim 12 wherein the nubs have a height in a range of about 0.05 to 0.065 inches.

15. In an unbonded capping system for compression testing of concrete cylinders, comprising retaining cups comprising metal blocks having a cylindrical cavity of a first select diameter for receiving one end of the concrete cylinder, and cylindrical compression pads each to be received in one of the retaining cup cavities to abut an end of the concrete cylinder, in use, and being of a second select diameter smaller than the first select diameter of the cavity to define a circumferential space therebetween, the improvement comprising:

means operatively associated with the compression pads for gripping the retaining cup cavity to prevent the compression pads from falling out of the cavities.

16. The improvement of claim 15 wherein the first and second compression pads comprise one piece neoprene pads.

17. The improvement of claim 15 wherein the first and second compression pads each comprises a cylindrical sidewall of the second select diameter and the gripping means comprises a plurality of circumferentially spaced nubs extending radially outwardly from the sidewall.

18. The improvement of claim 17 wherein the first select diameter is about 1/16 of an inch larger than the second select diameter.

19. The improvement of claim 18 wherein the nubs have a height of about 1/16 of an inch.

20. The improvement of claim 18 wherein the nubs have a height in a range of about 0.05 to 0.065 inches.

* * * * *